US00PP16025P2

(12) United States Plant Patent
Repp

(10) Patent No.: US PP16,025 P2
(45) Date of Patent: Oct. 4, 2005

(54) ***MANDEVILLA* PLANT NAMED 'COTTON CANDY'**

(50) Latin Name: ***Mandevilla* hybrid**
Varietal Denomination: Cotton Candy

(75) Inventor: Wanda Repp, Waynesville, NC (US)

(73) Assignee: Lake Area Nursery, Hawthorne, FL (US)

( * ) Notice: Subject to any disclaimer, the term of this patent is extended or adjusted under 35 U.S.C. 154(b) by 0 days.

(21) Appl. No.: 10/932,280

(22) Filed: Sep. 1, 2004

(51) Int. Cl.[7] ..... A01H 5/00
(52) U.S. Cl. ..... Plt./232
(58) Field of Search ..... Plt./232

*Primary Examiner*—Anne Marie Grunberg
(74) *Attorney, Agent, or Firm*—C. A. Whealy

(57) ABSTRACT

A new and distinct cultivar of *Mandevilla* plant named 'Cotton Candy', characterized by its upright vining growth habit; glossy, dark green-colored leaves; soft pink-colored flowers with imbricate petals with ruffled margins; and tolerance to low and high temperatures.

2 Drawing Sheets

Botanical classification/cultivar designation: *Mandevilla* hybrid cultivar Cotton Candy.

BACKGROUND OF THE INVENTION

The present Invention relates to a new and disctinct cultivar of *Mandevilla* plant, botanically known as *Mandevilla* hybrid, and hereinafter referred to by the name 'Cotton Candy'.

The new cultivar is a product of a planned breeding program conducted by the Inventor in Waynesville, N.C. The objective of the breeding program was to develop new *Mandevilla* cultivars with attractive flower form and coloration.

The new cultivar originated from a self-pollination of the *Mandevilla* hybrid cultivar Alice DuPont, not patented, in Waynesville, N.C. in June, 1998. The new cultivar was discovered and selected by the Inventor as a flowering plant within the progeny from this self-pollination in a controlled environment in Waynesville, N.C. in June, 1999. The new cultivar was selected on the basis of its flower form and flower coloration.

Asexual reproduction of the new cultivar by terminal cuttings in Hawthorne, Fla., since June, 2000, has shown that the unique features of this new *Mandevilla* are stable and reproduced true to type in successive generations.

SUMMARY OF THE INVENTION

Plants of the cultivar Cotton Candy have not been observed under all possible environmental conditions. The phenotype may vary somewhat with variations in environment such as temperature and light intensity without, however, any variance in genotype.

The following traits have been repeatedly observed and are determined to be the unique characteristics of 'Cotton Candy'. These characteristics in combination distinguish 'Cotton Candy' as a new and distinct cultivar:

1. Upright vining growth habit.
2. Glossy, dark green-colored leaves.
3. Soft pink-colored flowers with imbricate petals with ruffled margins.
4. Tolerant to low and high temperatures.

Plants of the new *Mandevilla* can be compared to plants of the parent cultivar, 'Alice DuPont'. In side-by-side comparisons conducted in Hawthorne, Fla., plants of the new *Mandevilla* differed from plants of the cultivar Alice DuPont in the following characteristics:

1. Leaves of plants of the new *Mandevilla* were smaller, smoother and glossier than leaves of plants of the cultivar Alice DuPont.
2. Plants of the new *Mandevilla* had smaller flowers than plants of the cultivar Alice DuPont.
3. Flower petals of plants of the new *Mandevilla* were lighter pink in color than flower petals of plants of the cultivar Alice DuPont.

Plants of the new *Mandevilla* can be compared to plants of the *Mandevilla* cultivar, 'Leah', not patented. In side-by-side comparisons conducted in Hawthorne, Fla., plants of the new *Mandevilla* differed from plants of the cultivar Leah in the following characteristics:

1. Leaves of plants of the new *Mandevilla* were glossier than leaves of plants of the cultivar Leah.
2. Plants of the new *Mandevilla* had smaller flowers than plants of the cultivar Leah.
3. Flower petals of plants of the new *Mandevilla* were lighter pink in color than flower petals of plants of the cultivar Leah.

Plants of the new *Mandevilla* can also be compared to plants of the *Mandevilla* cultivar, 'White Delight', disclosed in U.S. Plant Pat. No. 8,479. In side-by-side comparisons conducted in Hawthorne, Fla., plants of the new *Mandevilla* differed from plants of the cultivar White Delight in the following characteristics:

1. Leaves of plants of the new *Mandevilla* were broader than leaves of plants of the cultivar White Delight.
2. Flower petals of plants of the new *Mandevilla* were soft pink in color whereas flower petals of plants of the cultivar White Delight were whitish pink in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Mandevilla*.

The photograph on the first sheet comprises a side perspective view of a typical plant of 'Cotton Candy'.

The photograph on the second sheet is a close-up view of typical flowers and leaves of 'Cotton Candy'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were about one year old and grown in one-gallon containers in a polyethylene-covered greenhouse in Hawthorn, Fla. during the fall. During the production of the plants, day temperatures ranged from 32 to 35° C. and night temperatures were about 21° C..

Botanical classification: *Mandevilla* hybrid cultivar Cotton Candy.

Parentage: Self-pollination of *Mandevilla* hybrid cultivar Alice DuPont, not patented.

Propagation:

*Type.*—Terminal cuttings.

*Time to initiate roots, summer.*—About 20 to 30 days at 27° C.

*Time to initiate roots, winter.*—About 30 to 35 days at 21° C.

*Time to develop roots, summer.*—About 60 days at 27 to 32° C.

*Time to develop roots, winter.*—About 70 days at 24° C.

*Root description.*—Numerous, thick, fibrous and freely branching.

Plant description:

*Form.*—Perennial evergreen flowering plant; twining vine; initially upright, then vining, requires support to maintain upright habit. Plants are typically pinched about three months after planting to enhance lateral branch development; potentially two lateral branches form at every node.

*Plant height* (*length*).—About 77 cm.

*Plant diameter.*—About 24 cm.

*Vigor.*—Moderately vigorous.

*Lateral branches.*—Length: About 71 cm. Diameter: About 5 mm. Internode length: About 6 cm. Shape: Round in cross-section. Aspect: Initially upright, then trailing, requires support. Strength: Flexible, moderately strong. Texture: Developing stems, rough with very fine white pubescence. Mature stems, woody and mostly smooth and glabrous. Color: Developing stems: 144A. Mature stems: Close to 148A occasionally overlain with close to 165A to 165B.

*Foliage description.*—Leaves simple, opposite; generally symmetrical and long-persisting. Length: About 11 cm. Width: About 5 cm. Shape: Elongated oblong. Apex: Cuspidate. Base: Cordate. Margin: Entire. Texture, upper and lower surfaces: Rugose, leathery, durable; glabrous. Luster: Upper surface, glossy; lower surface, somewhat glossy to dull. Venation pattern: Pinnate. Petiole length: About 1 cm. Petiole diameter: About 4 mm. Petiole texture, upper surface: Slightly pubescent. Petiole texture, lower surface: Glabrous. Color: Developing and fully expanded foliage, upper surface: More green than 147A. Developing and fully expanded foliage, lower surface: Close to 147B to 146B. Venation, upper surface: Lateral veins, close to 147A; midvein, close to 146B. Venation, lower surface: Lateral veins, close to 146B; midvein, close to 150D. Petiole, upper and lower surfaces: Close to 146A to 146B.

Flower description:

*Flower type and habit.*—Single salverform flower; terminal or axillary; flowers face mostly outward. Flowers self-cleaning. Freely flowering, more than 30 flowers per plant develop during the flowering season.

*Natural flowering season.*—Spring until frost in the autumn; flowering continuous.

*Flower longevity on the plant.*—About four to five days.

*Fragrance.*—None detected.

*Flowers.*—Appearance: Flared trumpet, corolla fused, five-parted; petals imbricate; flowers roughly star-shaped. Diameter: About 9.4 cm. Depth (length): About 5.4 cm. Corolla tube length: About 3.8 cm. Throat diameter: About 2.5 cm. Tube diameter, base: About 4 mm.

*Flower buds* (*just before opening*).—Length: About 5.1 cm. Diameter: About 1.6 cm. Shape: Oblong. Color: Close to 155D underlain with close to 71A.

*Corolla.*—Arrangement/appearance: Single whorl of five petals, fused into flared trumpet; overlapping. Petal length: About 7.4 cm. Petal width: About 4 cm. Petal shape: Roughly spatulate. Petal apex: Acute with cuspidate tendencies. Petal margin: Entire; undulate, ruffled appearance. Petal texture, upper and lower surfaces: Smooth, velvety. Color: Petal, upper surface, when opening and fully opened: Close to 155D overlain with close to 71A. Petal, lower surface, when opening and fully opened: Close to 155D underlain with close to 71A. Tube, fully opened: Close to 155D underlain with close to 71A. Throat, fully opened: 9A to 9B.

*Sepals.*—Arrangement/appearance: Five per flower in a single whorl; fused; reflexed. Length: About 8 mm. Width: About 4 mm. Shape: Elongated, linear. Apex: Acuminate. Margin: Entire. Texture: Smooth, slightly waxy. Color, upper and lower surfaces: 144A to 144B; towards apex, overlain with close to 53A.

*Peduncles.*—Length: About 2.3 cm. Diameter: About 3 mm. Angle: Mostly straight. Strength: Flexible, but strong. Color: 144A.

*Reproductive organs.*—Stamens: Quantity: Five, filaments fused to corolla. Anther shape: Oblong, elongated. Anther size: About 6 mm by 2 mm. Anther color: 8C. Pollen: None observed. Pistils: Quantity: One. Pistile length: About 1.7 cm. Stigma shape: Rounded. Stigma color: Close to 150D. Style color: Close to 150D. Ovary color: Close to 144A to 144B.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to be tolerant to rain and wind and tolerant to temperatures from zero to higher than 38° C.

It is claimed:

1. A new and distinct cultivar of *Mandevilla* plant named 'Cotton Candy', as illustrated and described.

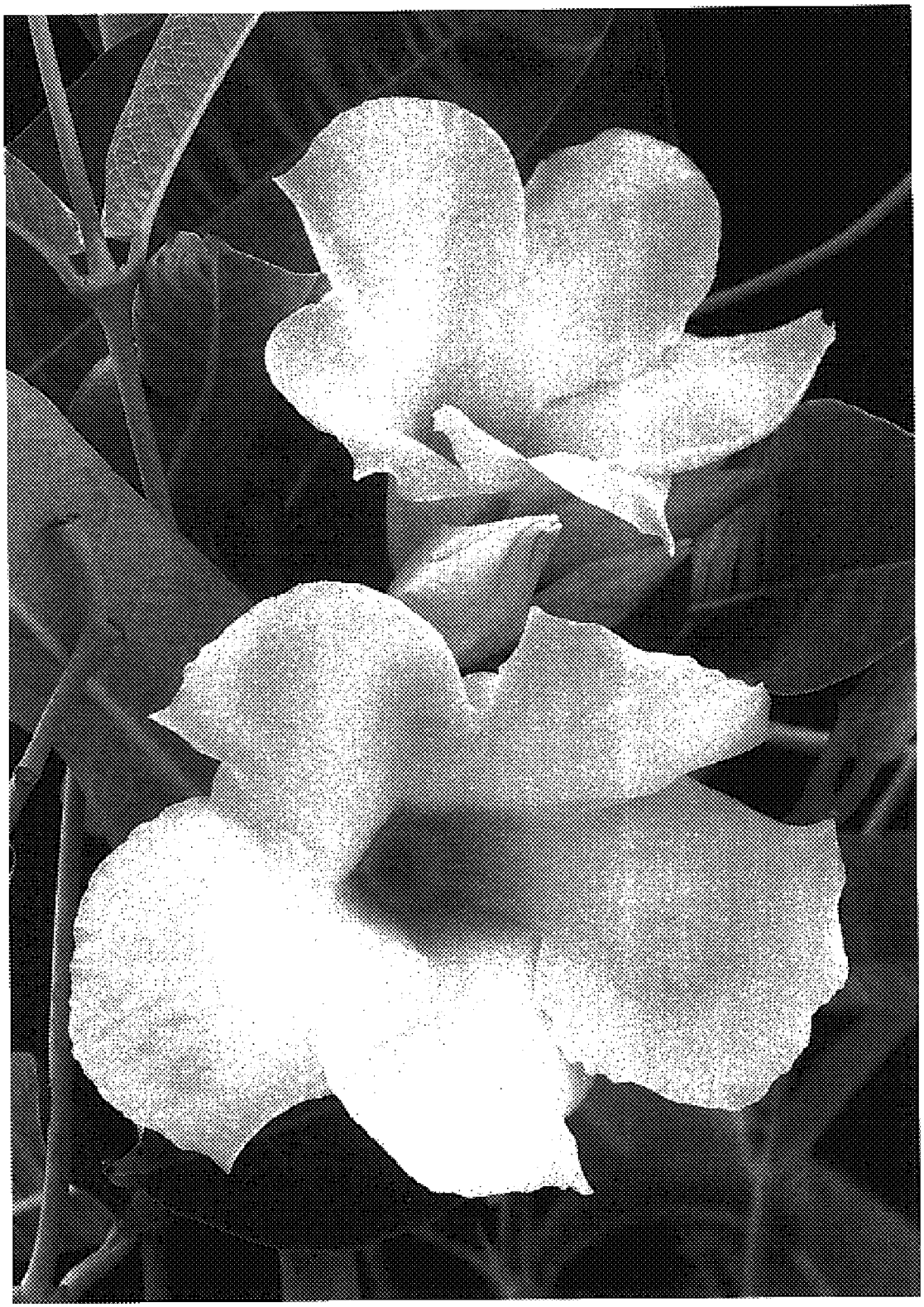

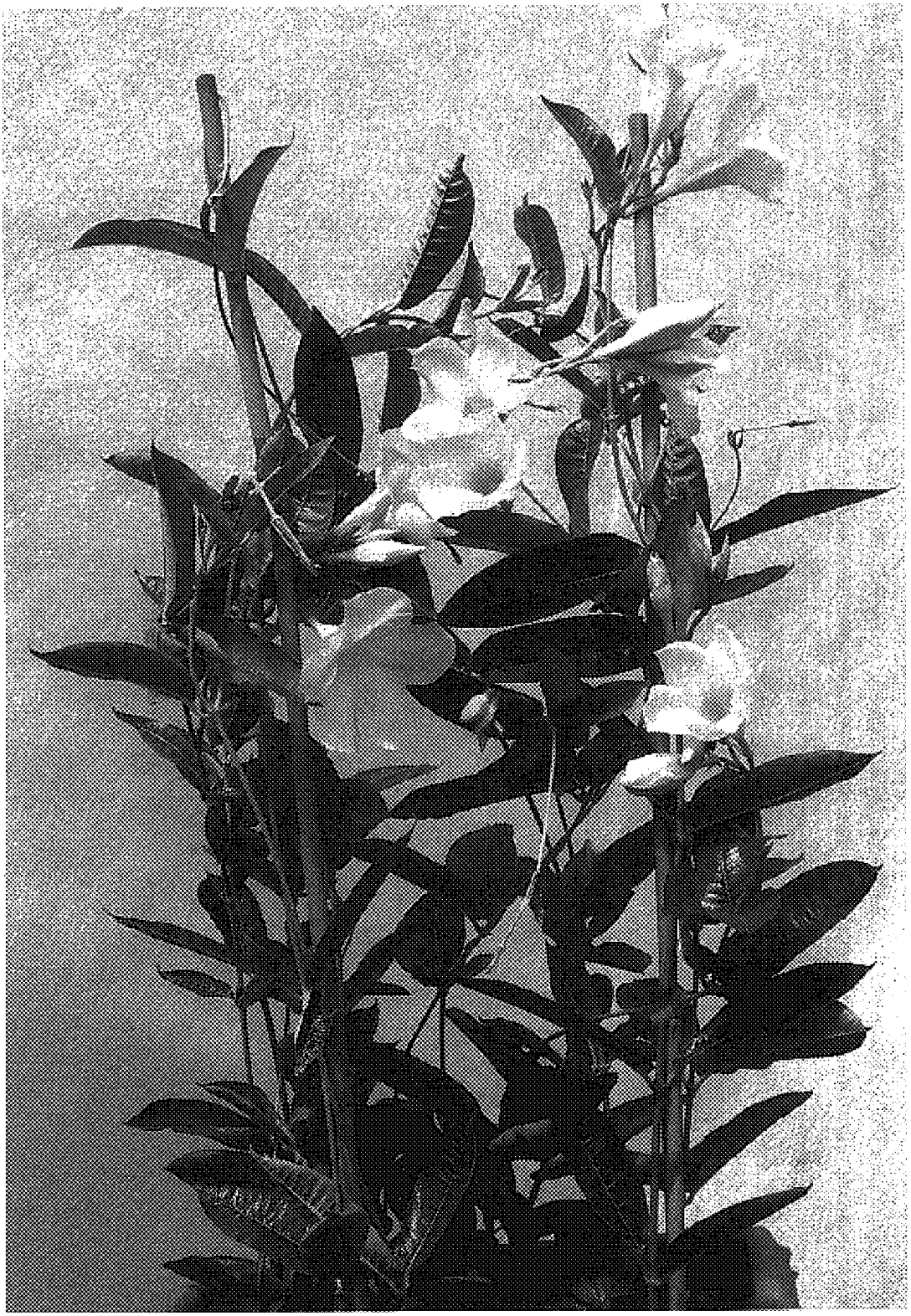

* * * * *